United States Patent
Park et al.

(10) Patent No.: US 9,572,769 B2
(45) Date of Patent: Feb. 21, 2017

(54) POLYMER-LIPOSOME NANOCOMPOSITE COMPOSITION FOR PERCUTANEOUS ABSORPTION, AND METHOD FOR PREPARING SAME

(75) Inventors: Sung Il Park, Seoul (KR); Youn Joon Kim, Seoul (KR); Sang Hoon Han, Suwon-si (KR)

(73) Assignee: Amorepacific Corporation (KR)

( * ) Notice: Subject to any disclaimer, the term of this patent is extended or adjusted under 35 U.S.C. 154(b) by 576 days.

(21) Appl. No.: 13/640,608

(22) PCT Filed: Apr. 12, 2011

(86) PCT No.: PCT/KR2011/002579
§ 371 (c)(1),
(2), (4) Date: Oct. 11, 2012

(87) PCT Pub. No.: WO2011/129588
PCT Pub. Date: Oct. 20, 2011

(65) Prior Publication Data
US 2013/0028951 A1 Jan. 31, 2013

(30) Foreign Application Priority Data
Apr. 13, 2010 (KR) .................. 10-2010-0033710

(51) Int. Cl.
| | | |
|---|---|---|
| *A61K 9/16* | (2006.01) |
| *A61K 9/50* | (2006.01) |
| *A61K 9/00* | (2006.01) |
| *A61K 8/14* | (2006.01) |
| *A61K 8/44* | (2006.01) |
| *A61K 9/127* | (2006.01) |
| *A61Q 19/02* | (2006.01) |
| *A61Q 19/08* | (2006.01) |
| *A61K 8/40* | (2006.01) |
| *A61K 8/55* | (2006.01) |
| *A61K 8/88* | (2006.01) |
| *A61K 8/02* | (2006.01) |
| *A61K 8/06* | (2006.01) |

(52) U.S. Cl.
CPC .......... *A61K 9/0014* (2013.01); *A61K 8/0295* (2013.01); *A61K 8/06* (2013.01); *A61K 8/14* (2013.01); *A61K 8/40* (2013.01); *A61K 8/44* (2013.01); *A61K 8/553* (2013.01); *A61K 8/88* (2013.01); *A61K 9/1271* (2013.01); *A61Q 19/02* (2013.01); *A61Q 19/08* (2013.01); *A61K 2800/413* (2013.01)

(58) Field of Classification Search
CPC ...... A61K 8/0241; A61K 8/0291; A61K 8/14; A61K 8/24; A61K 8/30; A61K 8/34; A61K 8/361; A61K 8/72; A61K 8/84; A61K 9/51; A61K 9/5107; A61K 9/5192; A61K 31/13

USPC .................................................. 424/464–495
See application file for complete search history.

(56) References Cited

U.S. PATENT DOCUMENTS

| | | | |
|---|---|---|---|
| 6,576,254 B1 | 6/2003 | Uchegbu | |
| 2004/0241222 A1* | 12/2004 | Metselaar | A61K 9/1271 424/450 |
| 2006/0293276 A1* | 12/2006 | Yedgar | A61K 31/685 514/54 |
| 2009/0016962 A1* | 1/2009 | Fukumura | A61K 47/48338 424/9.1 |

FOREIGN PATENT DOCUMENTS

| | | |
|---|---|---|
| EP | 1249232 B1 | 10/2006 |
| JP | H04202123 A | 7/1992 |
| JP | H04364195 A | 12/1992 |
| JP | 2004527585 A | 9/2004 |
| JP | 2004527586 A | 9/2004 |
| KR | 100422763 | 3/2004 |
| KR | 100463167 | 12/2004 |
| KR | 100530880 | 11/2005 |
| KR | 1020050117958 A | 12/2005 |
| KR | 100545836 | 1/2006 |
| KR | 100654102 B1 | 11/2006 |
| KR | 100654846 | 12/2006 |
| KR | 100716802 B1 | 5/2007 |
| KR | 100904370 | 6/2009 |
| WO | WO2005000258 A1 | 1/2005 |
| WO | 2005099889 A1 | 10/2005 |
| WO | 2007078060 A1 | 7/2007 |
| WO | 2007114262 A1 | 10/2007 |

OTHER PUBLICATIONS

Japanese Office Action dated Nov. 18, 2014 for Application No. JP2013-504817.
Chen et al., "Aggregation of biodegradable amphiphilic poly(succinimide-co-N-propyl aspartamide) and poly(N-dodecyl aspartamide-co-N-propyl aspartamide) in aqueous medium and its preliminary drug-released properties," Polymer, 46, 1821-1827 (Jan. 2005).
Suwa et al., "Self-Association Behavior of Hydrophobically Modified Poly(aspartic acid) in Water Studied by Flourescence and Dynamic Light Scattering Techniques," Macromolecules, 33, 7884-7892 (Sep. 2000).

\* cited by examiner

*Primary Examiner* — Micah-Paul Young
(74) *Attorney, Agent, or Firm* — Jansson Munger McKinley & Kirby Ltd.

(57) ABSTRACT

Provided are a polymer/liposome nanocomposite composition comprising lipids and poly(amino acids), and a method for preparing same. The polymer/liposome nanocomposite composition has excellent formation stability with respect to surfactants and salts, and can be used in various ways as a drug delivery system in the fields of medicine and cosmetics.

16 Claims, 2 Drawing Sheets

POLYMER-LIPOSOME NANOCOMPOSITE COMPOSITION FOR PERCUTANEOUS ABSORPTION, AND METHOD FOR PREPARING SAME

TECHNICAL FIELD

This disclosure relates to a polymer-liposome nanocomposite comprising a poly(amino acid) and a method for preparing the same.

BACKGROUND ART

Recently, utility of drug delivery systems using a liposome has been spotlighted. Thus, many attentions have been given to studies about preparation of more effective lipid-based nanocarriers through combination of various lipid components. Particularly, active studies have been conducted to provide a liposome formed from various components so that physiologically active ingredients incorporated into the inner phase of a liposome may be delivered to cells in vivo with high efficiency to realize their maximized efficiencies.

For example, some studies have been conducted about a liposome designed in such a manner that physiologically active ingredients incorporated into a liposome are released into cells through a decrease in liposome stability caused by the specific environment of a minute organ in cells. In addition, various systems capable of drug release at a predetermined temperature or pH range have been studied by using pH- or temperature-sensitive lipids or polymers in combination.

A liposome may include various types of lipid molecules but ensures no physical stability. Thus, many studies have been conducted to ensure liposome stability. In some technologies, a specific anionic surfactant is added to a liposome to induce an increase in stability. In other technologies, static charge lipids are added or sterols, anionic lipids or sphingolipids are introduced to elements forming a liposome. Further, it has been suggested that a liposome is mixed with an aqueous phase in which a polymeric emulsifier is dissolved, or a liposome is added to lamellar liquid crystals to stabilize physiologically active ingredients.

As mentioned above, active studies have been conducted continuously to improve the stability of a liposome or emulsion. However, the technologies according to the related art cannot provide sufficient physical stability, and thus are limited in use in the fields of food, cosmetics and pharmaceuticals.

In general, it is known that a liposome based on lipid-cholesterol does not ensure long-term stability in an aqueous phase. Particularly, such a liposome is highly liable to various salts used in vivo. To allow the use of such a liposome in cosmetics and skin application products, its stability in a formulation is required. However, such a liposome easily loses its structural integrity due to various surfactants present in a formulation.

DISCLOSURE

Technical Problem

This disclosure is directed to providing a polymer-liposome nanocomposite having excellent formulation stability.

This disclosure is also directed to providing a method for preparing a polymer-liposome nanocomposite.

Further, this disclosure is directed to providing a drug delivery system and composition for skin external application using a nanocomposite having excellent formulation stability.

Technical Solution

In one general aspect, there is provided a polymer-liposome nanocomposite, which is a nano-sized composite of a polymer and liposome and comprises a lipid and a poly(amino acid), wherein the poly(amino acid) is associated with a lipid bilayer containing the lipid.

In another general aspect, there is provided a method for preparing the above-mentioned polymer-liposome nanocomposite.

In still another general aspect, there is provided a composition for skin external application using the above-mentioned polymer-liposome nanocomposite.

Advantageous Effects

The polymer-liposome nanocomposite disclosed herein has excellent formulation stability against a surfactant and salt, and may be used widely in the fields of pharmaceuticals and cosmetics.

BEST MODE

Figure 1:
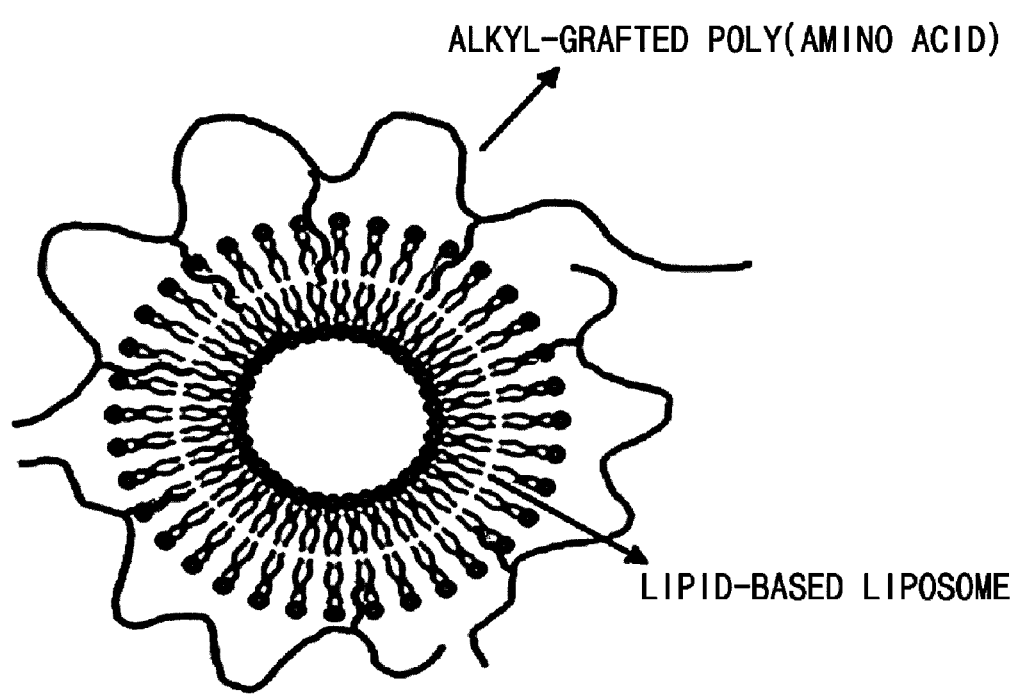
FIG. 1 is a schematic view showing the polymer-liposome nanocomposite according to an embodiment.

The polymer-liposome nanocomposite disclosed herein is a nano-sized composite of a polymer and liposome and comprises a lipid and a poly(amino acid), wherein the poly(amino acid) is associated with a lipid bilayer containing the lipid. An illustrative embodiment of the structure of the polymer-liposome nanocomposite is shown in FIG. 1.

In addition, the polymer-liposome nanocomposite may further comprise cholesterol. Addition of cholesterol interrupts self-association capability of the lipid-polymer bilayer but improves the curvature of liposome, thereby facilitating formation of a stable spherical liposome.

The lipid used in the polymer-liposome nanocomposite disclosed herein may be a phospholipid or nitrolipid having a $C_{12}$-$C_{24}$ fatty acid chain, particularly phospholipid. Particular examples of the lipid may be at least one selected from the group consisting of: one or more natural phospholipids selected from the group consisting of egg yolk lecithin (phosphatidyl choline), soybean lecithin, lysolecithin, sphingomyelin, phosphatidic acid, phosphatidyl serine, phosphatidyl glycerol, phosphatidyl inositol, phosphatidyl ethanol amine, diphosphatidyl glycerol, cardiolipin and plasmalogen; one or more synthetic lipids selected from the group consisting of dicetyl phosphate, distearoyl phosphatidyl choline, dioleoylphosphatidyl ethanol amine, dipalmitoyl phosphatidyl choline, dipalmitoyl phosphatidyl ethanol amine, dipalmitoyl phosphatidyl serine, eleostearoyl phosphatidyl choline, eleostearoyl phosphatidyl ethanol amine and eleostearoyl phosphatidyl serine; hydrogenated products that may be obtained from the natural phospholipids or synthetic lipids; derivatives of the natural phospholipids or synthetic lipids; and fatty acid mixtures that may be obtained by hydrolysis of the natural phospholipids or synthetic lipids. The lipids, including phospholipids or the like, may be used alone or in combination.

The poly(amino acid) used in the polymer-liposome nanocomposite disclosed herein associates with a lipid or lipid/cholesterol bilayer while binding the bilayer tightly, and serves to protect the outer shell of a liposome so that the structure of a liposome is maintained stably against various factors (e.g. a salt, surfactant) present in an aqueous phase and unstabilizing the liposome structure. By virtue of this, it is possible to maintain stably various formulations of a composition for skin external application or cosmetic composition. According to an embodiment, the poly(amino acid) may be a random copolymer containing an amino acid such as aspartic acid or asparagine, or an amino acid derivative such as hydroxyethyl aspartamide. Particularly, the poly(amino acid) may be poly(aspartic acid) or poly(asparagine).

In addition, the poly(amino acid) may be a lipid-containing poly(amino acid), particularly a random copolymer of lipid-grafted amino acid or amino acid derivative. According to an embodiment, the poly(amino acid) may be an n-alkyl asparagine introduced to allow association with a lipid bilayer, wherein the range of n that represents the length of an alkyl chain is determined according to the type of a lipid that participates in association. Particularly, when the alkyl chain has at least 8 carbon atoms (octyl or higher alkyl), n-alkyl aspartic acid is capable of association with a lipid or lipid/cholesterol bilayer. For example, the carbon number, n, may be an integer of 12-22. If desired, instead of the n-alkyl chain, cholesterol or a lipid component such as phytosphingosine may be grafted onto the polymer to accomplish association with a lipid bilayer. According to an embodiment, the poly(amino acid) may be a copolymer of asparagine with n-alkyl asparagine. For example, the poly(amino acid) may be an amphiphilic polyasparagine onto which an alkyl chain is grafted as depicted in the following Chemical Formula 1:

[Chemical Formula 1]

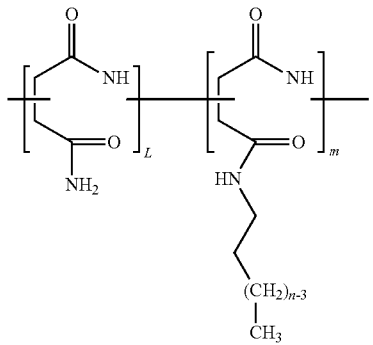

wherein n is an integer of 8 or more, particularly an integer of 12-36; and

L and m are not particularly limited, but each is within a range of 1-1000 per mole of the polymer. When the poly(amino acid) has an excessively low molecular weight, it is not possible to obtain a stabilization effect. On the other hand, when the poly(amino acid) has an excessively high molecular weight, the polymer itself forms an associated structure, thereby making it difficult to form a liposome associated with a lipid.

In addition, the lipid in the lipid-grafted poly(amino acid) may include at least one selected from the group consisting of phospholipids, sphingolipids and sterols, and has a meaning that covers any monomers whose fatty alcohol or fatty acid has an aliphatic chain of $C_8$ or higher, particularly $C_{12}$-$C_{36}$. The poly(amino acid) may be present in the polymer-liposome nanocomposite in an amount of 0.5-50 wt %, particularly 1.0-30 wt %, and more particularly 5.0-20 wt % based on the total weight of the polymer-liposome nanocomposite. When the poly(amino acid) is present in an amount greater than 50 wt %, it is not possible to obtain a desired bilayer-structured polymer-liposome formulation. On the other hand, when the poly(amino acid) is present in an amount less than 0.5 wt %, the polymer may not realize a desired effect of stabilizing a liposome. The poly(amino acid) may have a number average molecular weight of 1,000-200,000 (Dalton), particularly 5,000-50,000. When the polymer has a molecular weight greater than 200,000, association with liposome may be degraded. On the other hand, when the polymer has a molecular weight less than 1,000, an effect of stabilizing a liposome may be degraded.

The polymer-liposome nanocomposite disclosed herein has a nano-scaled size. For example, the polymer-liposome nanocomposite may have a particle size of 50-300 nm. This is required for providing a liposome with a stable structure. In addition, the particle size may be varied with the polymer composition or concentrations of the polymer and lipid.

In addition, the cholesterol used in the polymer-liposome nanocomposite may be added in an amount of 50% or less based on the lipid content. When the cholesterol is used in an excessively large amount, it is difficult for a liposome to form a bilayer membrane structure.

In another aspect, there is provided a method for preparing the polymer-liposome nanocomposite.

Particularly, the method for preparing a polymer-liposome nanocomposite comprises:

mixing and dissolving a lipid, cholesterol or fatty alcohol, and a fatty acid in an organic solvent, and allowing the solvent to evaporate to obtain a lipid mixture;

adding an aqueous solution containing a lipid-grafted poly(amino acid) dissolved therein to the lipid mixture to obtain a mixed solution; and forming microparticles from the particles of a composite formed in the mixed solution.

The lipid component used in the polymer-liposome nanocomposite may be a phospholipid or nitrolipid having a $C_{12}$-$C_{24}$ fatty acid chain. In general, a phospholipid may be used. Cholesterol may be added thereto as necessary.

In addition, the poly(amino acid) may be a lipid-grafted poly(amino acid). According to another embodiment, the poly(amino acid) may be an n-alkyl chain-grafted asparagine, wherein the range of n that represents the length of an alkyl chain is determined according to the type of a lipid that participates in association. If desired, instead of the n-alkyl chain, cholesterol or a lipid component such as phytosphingosine may be introduced to the polymer. Further, the operation of forming microparticles may be carried out by a high-pressure emulsifier or ultrasonic treatment, but is not limited thereto.

In mixing and dissolving a lipid, cholesterol or fatty alcohol, and a fatty acid, the solvent may be ethyl alcohol, methylene chloride or chloroform.

A particular embodiment of the method for preparing a polymer-liposome nanocomposite will be described hereinafter.

First, L-aspartic acid and phosphoric acid as an acid catalyst are introduced to mesitylene or sulfolane as a solvent, and allowed to react by maintaining the reaction mixture at 180° C. for about 10 hours under nitrogen atmosphere, thereby providing polycondensed poly(succinimide). The polycondensed poly(succinimide) may have a different molecular weight as a function of the reaction solvent. The polycondensed poly(succinimide) is washed with methanol and purified water and dried to obtain a powdery polymer. The resultant powdery polymer is mixed with an alkyl amine in dimethyl formamide as a solvent and allowed to react at 70° C. for 24 hours. Then, 5N aqueous ammonium hydroxide ($NH_4OH$) solution is added dropwise thereto at room temperature to perform hydrolysis, and an excessive amount of ether is used to cause precipitation. The resultant precipitate is dried to obtain an alkyl group-grafted amphiphilic poly(amino acid).

A liposome may be obtained by a thin film forming method using ultrasonic waves. A lipid component such as distearoylphosphatidylcholine is dissolved in chloroform ($CHCl_3$) in a round neck flask and the solvent is removed in a rotary evaporator to form a thin lipid membrane on the wall surface of the flask. Then, water containing the amphiphilic poly(amino acid) dissolved therein is added thereto to perform hydration, followed by ultrasonic treatment, thereby providing a polymer-liposome nanocomposite.

In addition, the polymer-liposome nanocomposite disclosed herein may further include a physiologically active ingredient incorporated thereto. For example, when the active ingredient incorporated into the polymer-liposome nanocomposite is a pharmaceutically active ingredient, the polymer-liposome nanocomposite may serve as a drug delivery system.

The physiologically active ingredient incorporated into the polymer-liposome nanocomposite is not particularly limited but may be a water-soluble ingredient. Particularly, active ingredients related to whitening, anti-oxidation and/or anti-wrinkle may be used. For example, the active ingredients may include those known as whitening agents, such as N-butyldeoxynojirimycin, 1-deoxynojirimycin, castanospermin, streptomyces culture extract (SCE), calcium pentatheine sulfonate, albutin, vitamin C (ascorbic acid), vitamin C derivatives such as ethylascorbyl ether, and those known as anti-wrinkle agents, such as oleanolic acid, retinol, alpha-ketoglutaric acid, epigallocatechin gallate (EGCG).

In still another aspect, there is provided a composition for skin external application including the polymer-liposome nanocomposite. In addition, the polymer-liposome nanocomposite used in the composition for skin external application may further include at least one of the above-listed physiologically active ingredients. The composition for skin external application may be a skin whitening, anti-oxidative and/or anti-wrinkle composition. The composition for skin external application is not particularly limited in its formulation, and may be provided as a liposome, emulsion or liquid crystal form.

The examples and experiments will now be described. The following examples and experiments are for illustrative purposes only and not intended to limit the scope of this disclosure.

REFERENCE EXAMPLE 1

Preparation of Amphiphilic Poly(Amino Acid)

First, 250 g of L-aspartic acid and 3 mL of phosphoric acid (85%) are introduced to 250 g of sulfolane, and allowed to stand at 180° C. for about 10 hours to carry out a reaction. The resultant polycondensed poly(succinimide) is washed several times by using methanol and purified water alternately. Then, 1 g of the resultant powdery polymer is mixed with 0.1 g of alkyl amine in dimethylformamide solvent to carry out a reaction at 70° C. for 24 hours. Then, 5N aqueous ammonium hydroxide ($NH_4OH$) solution is added dropwise thereto and the mixture is agitated at room temperature for 3 hours to perform hydrolysis. An excessive amount of ethyl ether is added thereto to cause precipitation and the precipitate is dried to obtain an alkyl group-grafted amphiphilic poly(amino acid) polymer.

EXAMPLE 1

Preparation of Polymer-Liposome Nanocomposite Using Dodecyl Group-Grafted Poly(Amino Acid)

First, 1 g of 100% hydrogenated oleoyl-palmitoyl/oleoyl-stearyl phosphatidylcholine mixture (Lipoid S100-3) is introduced to a round neck flask and dissolved into chloroform ($CHCl_3$) therein. The solvent is removed by a rotary evaporator to form a thin lipid membrane on the wall surface of the flask. Then, 50 mL of water containing 0.1 g of the amphiphilic poly(dodecyl-asparagine) copolymer obtained by using dodecyl amine as an alkyl amine in Reference Example 1 is added thereto to perform hydration at 65° C. Then, ultrasonic treatment is carried out to obtain a polymer-liposome nanocomposite.

The phospholipid mixture used in this example has the composition as shown in the following Table 1.

TABLE 1

| Ingredients | wt % |
|---|---|
| Phosphatidyl choline | >96 |
| Phosphorus compound | 3.7-4.0 |
| Ethanol | 0-1.0 |
| Water | 0-2.0 |

EXAMPLE 2

Preparation of Polymer-Liposome Nanocomposite Using Octadecyl Group-Grafted Poly(Amino Acid)

First, 1 g of 100% hydrogenated oleoyl-palmitoyl/oleoyl-stearyl phosphatidylcholine mixture (Lipoid S100-3) is introduced to a round neck flask and dissolved into chloroform ($CHCl_3$) therein. The solvent is removed by a rotary evaporator to form a thin lipid membrane on the wall surface of the flask. Then, 50 mL of water containing 0.1 g of the amphiphilic poly(octadecyl-asparagine) copolymer obtained by using octadecyl amine as an alkyl amine in Reference Example 1 is added thereto to perform hydration at 70° C. Then, ultrasonic treatment is carried out to obtain a polymer-liposome nanocomposite.

The phospholipid mixture used in this example has the composition as shown in the above Table 1.

COMPARATIVE EXAMPLE 1

Preparation of Simple Lipid-Based Liposome

To compare the structure and properties in a solution of a polymer-liposome composite using a biodegradable polymer with those of a lipid-based conventional liposome, a simple lipid-based liposome is prepared. First, 1 g of 100% hydrogenated oleoyl-palmitoyl/oleoyl-stearyl phosphatidylcholine mixture (Lipoid S100-3) is introduced to a round neck flask and dissolved into chloroform (CHCl$_3$) therein. The solvent is removed by a rotary evaporator to form a thin lipid membrane on the wall surface of the flask. Then, 50 mL of water is added thereto to perform hydration at 65° C. Then, ultrasonic treatment is carried out to obtain a liposome.

COMPARATIVE EXAMPLE 2

Preparation of Lipid-Cholesterol Mixed Liposome

First, 1 g of 100% hydrogenated oleoyl-palmitoyl/oleoyl-stearyl phosphatidylcholine mixture (Lipoid S100-3) and 0.05 g of cholesterol are introduced to a round neck flask and dissolved into chloroform (CHCl$_3$) therein. The solvent is removed by a rotary evaporator to form a thin lipid membrane on the wall surface of the flask. Then, 50 mL of water is added thereto to perform hydration at 65° C. Then, ultrasonic treatment is carried out to obtain a liposome.

COMPARATIVE EXAMPLE 3

Preparation of Lipid-Fatty Alcohol Mixed Liposome

First, 1 g of 100% hydrogenated oleoyl-palmitoyl/oleoyl-stearyl phosphatidylcholine mixture (Lipoid S100-3) and 0.1 g of stearyl alcohol are introduced to a round neck flask and dissolved into chloroform (CHCl$_3$) therein. The solvent is removed by a rotary evaporator to form a thin lipid membrane on the wall surface of the flask. Then, 50 mL of water is added thereto to perform hydration at 70° C. Then, ultrasonic treatment is carried out to obtain a liposome.

TEST EXAMPLE 1

Test for Determining Stability of Lipid Lamella Composition Stabilized with Poly(Amino Acid)

A test is carried out to determine the stability of each of the liposomes obtained from Examples 1 and 2 and Comparative Examples 1-3 against a surfactant.

A surfactant, deoxycholic acid, is added to each liposome solution according to the above Examples and Comparative Examples at a molar ratio of 0.01-100 based on the lipid contained in the liposome solution. Then, absorbance is measured at 405 nm to determine the degree of decomposition of each liposome.

Figure 2:
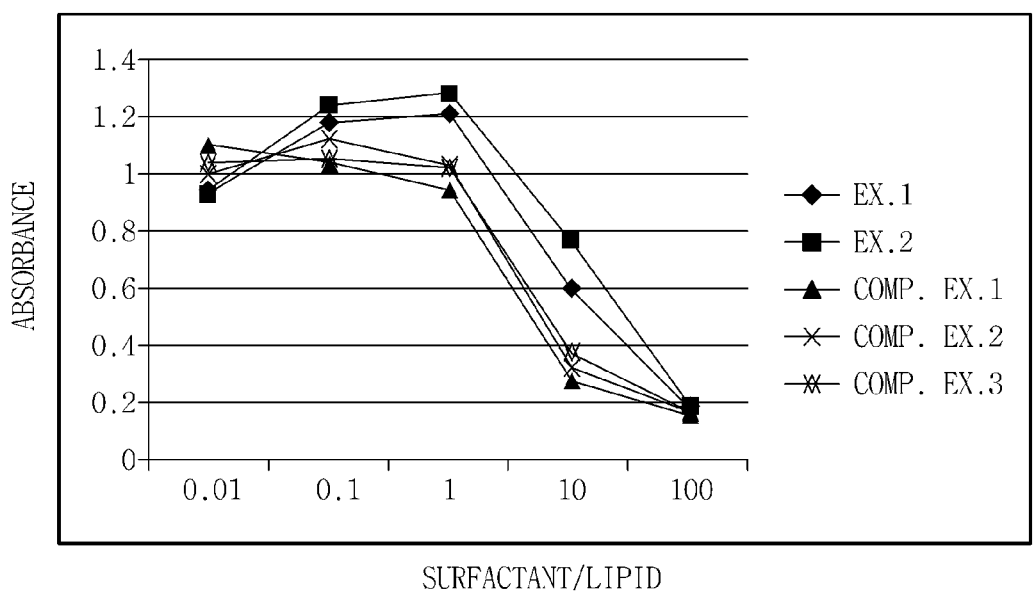
FIG. 2 is a graph showing the results of absorbance measurement as a function of the amount of a surfactant added to a liposome in a test for determining the degree of decomposition of a liposome.

FIG. 2 shows the results of absorbance measurement as a function of the amount of a surfactant added to a liposome in a test for determining the degree of decomposition of a liposome. In addition, the amount of a surfactant required to decompose 50% of each liposome is shown in the following Table 2 as a relative amount when the amount of a surfactant in the case of a solution containing a phospholipid alone is taken as 1.

TABLE 2

| | Amount of Surfactant (%) |
|---|---|
| Ex. 1 | 2.3 |
| Ex. 2 | 3.2 |
| Comp. Ex. 1 | 1.0 |
| Comp. Ex. 2 | 1.2 |
| Comp. Ex. 3 | 1.4 |

Referring to Table 2 and FIG. 2, it can be seen that a relatively larger amount of surfactant is required to decompose 50% of the liposome according to Examples 1 and 2, as compared with Comparative Examples. Particularly, in the case of Example 2, a surfactant is required in an amount at least three times higher than Comparative Example 1. This suggests that the composition disclosed herein has significantly improved stability against a surfactant.

When comparing Example 1 with Example 2, it can be seen that use of a longer alkyl chain grafted onto the polymer stabilizes the liposome structure better than a shorter alkyl chain. It is thought that a longer alkyl chain has stronger hydrophobic interaction with a liposome bilayer membrane, and thus is bound physically with the lipid bilayer membrane more strongly than a shorter alkyl chain.

It can be seen from this test example that the polymer-lipid nanocomposite composition disclosed herein has higher stability in a formulation containing a surfactant as compared to a conventional lipid-based liposome. Thus, it is expected that the polymer-lipid nanocomposite disclosed herein may be applied widely to stabilization of various functional materials, which, otherwise, cannot be used in an aqueous phase or mixture due to the lack of stability.

TEST EXAMPLE 2

Evaluation of Stability of Polymer-Liposome Nanocomposite

The polymer-liposome nanocomposites according to Examples 1 and 2 and Comparative Examples 1 and 3 and a lipid-based liposome are evaluated for their long-term stabilities in an aqueous solution containing a salt. Particularly, particle sizes are determined as a function of time in a solution using sodium phosphate buffer instead of water. The results are shown in the following Table 3.

TABLE 3

| | Particle Size (nm) (Polydispersity) | | | | |
|---|---|---|---|---|---|
| | Upon preparation | 1 week | 2 weeks | 3 weeks | 4 weeks |
| Ex. 1 | 153 (0.03) | 158 (0.15) | 161 (0.13) | 162 (0.16) | 164 (0.17) |
| Ex. 2 | 157 (0.02) | 159 (0.13) | 162 (0.12) | 163 (0.16) | 165 (0.15) |
| Comp. Ex. 1 | 207 (0.38) | 232 (0.4) | precipitation | precipitation | precipitation |
| Comp. Ex. 3 | 189 (0.31) | 195 (0.35) | 199 (0.38) | 201 (0.4) | 203 (0.42) |

As can be seen from Table 3, the polymer-liposome nanocomposites cause no significant difference in particle size or polydispersity even after storing them in a buffer solution containing a salt. On the contrary, in the case of the lipid-based liposome (Comparative Example 1), it causes an increase in particle size and polydispersity in a sodium phosphate buffer solution, leading to an unstable structure. In addition, in the case of the liposome merely using hydrogenated lecithin without any additives, the liposome structure is broken and precipitation occurs after 2 weeks. This suggests that the polymer-liposome nanocomposites maintain more stable structures in the presence of other salts in an aqueous solution as compared to the lipid-based liposome.

The invention claimed is:
1. A polymer-liposome nanocomposite, which is a nano-sized composite of a polymer and liposome and comprises a lipid and an alkyl-grafted poly(amino acid), wherein the alkyl-grafted poly(amino acid) is associated with a lipid bilayer containing the lipid, wherein the alkyl-grafted poly(amino acid) is selected from the group consisting of poly(aspartic acid) and poly(asparagine) units, wherein the alkyl grafted onto the alkyl-grafted poly (amino acid) has an aliphatic chain having at least 8 carbon atoms, and is combined at side chains of the alkyl-grafted poly(amino acid), and wherein the alkyl-grafted poly(amino acid) comprises 2 to 1000 alkyl-grafted amino acid units and 1 to 1000 non-alkyl-grafted amino acid units per mole of the polymer.

2. The polymer-liposome nanocomposite according to claim 1, which further comprises cholesterol.

3. The polymer-liposome nanocomposite according to claim 1, wherein the lipid is a phospholipid or nitrolipid having a $C_{12}$-$C_{24}$ fatty acid chain.

4. The polymer-liposome nanocomposite according to claim 3, wherein the lipid is at least one selected from the group consisting of:

one or more natural phospholipids selected from the group consisting of egg yolk lecithin (phosphatidyl choline), soybean lecithin, lysolecithin, sphingomyelin, phosphatidic acid, phosphatidyl serine, phosphatidyl glycerol, phosphatidyl inositol, phosphatidyl ethanol amine, diphosphatidyl glycerol, cardiolipin and plasmalogen;

one or more synthetic lipids selected from the group consisting of dicetyl phosphate, distearoyl phosphatidyl choline, dioleoylphosphatidyl ethanol amine, dipalmitoyl phosphatidyl choline, dipalmitoyl phosphatidyl ethanol amine, dipalmitoyl phosphatidyl serine, eleostearoyl phosphatidyl choline, eleostearoyl phosphatidyl ethanol amine and eleostearoyl phosphatidyl serine;

hydrogenated products obtainable from the natural phospholipids or synthetic lipids;

derivatives of the natural phospholipids or synthetic lipids; and fatty acid mixtures obtainable by hydrolysis of the natural phospholipids or synthetic lipids.

5. The polymer-liposome nanocomposite according to claim 1, wherein the alkyl-grafted poly(amino acid) is present in an amount of 0.5-50 wt % based on the total weight of the polymer-liposome nanocomposite.

6. The polymer-liposome nanocomposite according to claim 1, wherein the alkyl-grafted poly(amino acid) has a number average molecular weight of 1,000-200,000 (Dalton).

7. The polymer-liposome nanocomposite according to claim 1, wherein the nanocomposite has a size of 50-300 nm.

8. A method for preparing a polymer-liposome nanocomposite according to claim 1, comprising:

mixing and dissolving a lipid, cholesterol or fatty alcohol, and a fatty acid in an organic solvent, and allowing the solvent to evaporate to obtain a lipid mixture;

adding an aqueous solution containing an alkyl-grafted poly(amino acid) dissolved therein to the lipid mixture to obtain a mixed solution; and forming microparticles from the particles of a composite formed in the mixed solution.

9. The method according to claim 8, wherein said forming microparticles is carried out by a high-pressure emulsifier or through ultrasonic treatment.

10. The polymer-liposome nanocomposite according to claim 1, which is for use in drug delivery systems.

11. A composition for skin external application comprising the polymer-liposome nanocomposite as defined in claim 1.

12. The composition for skin external application according to claim 11, wherein the polymer-liposome nanocomposite further comprises, as a physiologically active ingredient, at least one selected from the group consisting of N-butyldeoxynojirimycin, 1-deoxynojirimycin, castanospermin, streptomyces culture extract (SCE), calcium pentatheine sulfonate, albutin, vitamin C (ascorbic acid), ethylascorbyl ether, alpha-ketoglutaric acid, eanolic acid, retinol and epigallocatechin gallate (EGCG).

13. The composition for skin external application according to claim 11, which is formulated into a liposome, emulsion or liquid crystal.

14. The composition for skin external application according to claim 11, which is for use in skin whitening, antioxidation or anti-wrinkle.

15. A method for delivering drugs comprising administering an effective amount of the polymer-liposome nanocomposite according to claim 1 to a subject in such need, wherein the method is for delivering drugs.

16. A method for skin whitening, antioxidation or anti-wrinkle comprising administering an effective amount of the composition according to claim 11 to a subject in such need, wherein the method is for skin whitening, antioxidation or anti-wrinkle.

* * * * *